US011555017B2

United States Patent
Fadli

(10) Patent No.: US 11,555,017 B2
(45) Date of Patent: Jan. 17, 2023

(54) OXIDATION BASE DERIVED FROM 1-HEXYL-4,5-DIAMINOPYRAZOLE, COMPOSITION CONTAINING SAME AND USE THEREOF IN OXIDATION DYEING OF KERATIN FIBRES

(71) Applicant: L'Oreal, Paris (FR)

(72) Inventor: Aziz Fadli, Aulnay-sous-Bois (FR)

(73) Assignee: L'OREAL, Paris (FR)

( * ) Notice: Subject to any disclaimer, the term of this patent is extended or adjusted under 35 U.S.C. 154(b) by 202 days.

(21) Appl. No.: 16/095,816

(22) PCT Filed: May 24, 2017

(86) PCT No.: PCT/EP2017/062492
§ 371 (c)(1),
(2) Date: Oct. 23, 2018

(87) PCT Pub. No.: WO2017/202884
PCT Pub. Date: Nov. 30, 2017

(65) Prior Publication Data
US 2020/0392088 A1    Dec. 17, 2020

(30) Foreign Application Priority Data
May 25, 2016    (FR) ........................ 1654682

(51) Int. Cl.
*A61K 8/49*    (2006.01)
*A61Q 5/10*    (2006.01)
*C07D 231/38*    (2006.01)

(52) U.S. Cl.
CPC ............ *C07D 231/38* (2013.01); *A61K 8/494* (2013.01); *A61Q 5/10* (2013.01); *A61K 2800/10* (2013.01); *A61K 2800/4324* (2013.01); *A61K 2800/87* (2013.01); *A61K 2800/882* (2013.01); *A61K 2800/884* (2013.01)

(58) Field of Classification Search
None
See application file for complete search history.

(56) References Cited

U.S. PATENT DOCUMENTS

| | | | |
|---|---|---|---|
| 4,003,699 | A | 1/1977 | Rose et al. |
| RE30,199 | E | 1/1980 | Rose et al. |
| 4,823,985 | A | 4/1989 | Grollier et al. |
| 5,061,289 | A | 10/1991 | Clausen et al. |
| 5,380,340 | A | 1/1995 | Neunhoeffer et al. |
| 5,534,267 | A | 7/1996 | Neunhoeffer et al. |
| 5,663,366 | A | 9/1997 | Neunhoeffer et al. |
| 5,718,731 | A | 2/1998 | Loewe et al. |
| 5,766,576 | A | 6/1998 | Lowe et al. |
| 6,099,592 | A | 8/2000 | Vidal et al. |
| 6,284,003 | B1 | 9/2001 | Rose et al. |
| 6,730,789 | B1 | 5/2004 | Birault et al. |
| 2001/0009044 | A1 | 7/2001 | Braun |
| 2002/0040508 | A1 | 4/2002 | Vidal et al. |
| 2007/0202282 | A1 | 8/2007 | Fujie et al. |
| 2008/0012929 | A1 | 1/2008 | Fujie et al. |
| 2012/0210519 | A1 | 8/2012 | Lim et al. |
| 2012/0210520 | A1 | 8/2012 | Lim et al. |
| 2012/0210521 | A1 | 8/2012 | Lim et al. |
| 2012/0210522 | A1 | 8/2012 | Lim et al. |
| 2012/0210524 | A1 | 8/2012 | Lim et al. |

(Continued)

FOREIGN PATENT DOCUMENTS

| | | |
|---|---|---|
| DE | 2359399 A1 | 6/1975 |
| DE | 3843892 A1 | 6/1990 |
| DE | 4133957 A1 | 4/1993 |
| DE | 19543988 A1 | 5/1997 |
| EP | 0375977 A1 | 7/1990 |
| EP | 0692246 A1 | 1/1996 |
| EP | 0714954 A2 | 6/1996 |
| EP | 0770375 A1 | 5/1997 |
| FR | 2586913 A1 | 3/1987 |
| FR | 2763241 A1 | 11/1988 |

(Continued)

OTHER PUBLICATIONS

International Search Report and Written Opinion for counterpart Application No. PCT/EP2017/062492, dated Aug. 3, 2017.

*Primary Examiner* — Jennifer A Berrios
(74) *Attorney, Agent, or Firm* — The Marbury Law Group, PLLC

(57) ABSTRACT

The present invention relates to novel 1-hexyl-1H-pyrazole-4,5-diamine derivative compounds of formula (I), to a composition for oxidation dyeing of the keratin fibres containing same, to a process for preparing the compounds of formula (I), to reaction intermediates, to an oxidation dyeing process using the composition, to the use of the compounds of formula (I) for oxidation dyeing of keratin fibres, and also to a kit; and
to the 1-hexyl-4,5-diaminopyrazole derivative compounds of formula (I) below:

(I)

and also the addition salts thereof with organic or mineral acids, the tautomers thereof, and the solvates thereof such as hydrates, in which ALK is as defined in the description.

20 Claims, No Drawings

(56) References Cited

U.S. PATENT DOCUMENTS

2012/0210525 A1    8/2012   Lim et al.
2012/0210526 A1    8/2012   Lim et al.

FOREIGN PATENT DOCUMENTS

| | | |
|---|---|---|
| FR | 2733749 A1 | 11/1996 |
| FR | 2801308 A1 | 5/2001 |
| FR | 2886136 A1 | 12/2006 |
| GB | 1026978 A | 4/1966 |
| GB | 1153196 A | 5/1969 |
| JP | 02-019576 A | 1/1990 |
| JP | 05-163124 A | 6/1993 |
| WO | 94/08969 A1 | 4/1994 |
| WO | 94/08970 A1 | 4/1994 |
| WO | 95/01772 A1 | 1/1995 |
| WO | 95/15144 A1 | 6/1995 |
| WO | 96/15765 A1 | 5/1996 |
| WO | 98/17234 A1 | 4/1998 |
| WO | 98/20847 A1 | 5/1998 |
| WO | WO2009140451 * | 11/2009 |
| WO | 2013/122989 A1 | 8/2013 |
| WO | 2013/122990 A1 | 8/2013 |

\* cited by examiner

OXIDATION BASE DERIVED FROM 1-HEXYL-4,5-DIAMINOPYRAZOLE, COMPOSITION CONTAINING SAME AND USE THEREOF IN OXIDATION DYEING OF KERATIN FIBRES

CROSS REFERENCE TO RELATED APPLICATIONS

This is a national stage application of PCT/EP2017/062492, filed internationally on May 24, 2017, which claims priority to French Application No. 1654682, filed on May 25, 2016, both of which are incorporated by reference herein in their entireties.

The present invention relates to novel 1-hexyl-1H-pyrazole-4,5-diamine derivative compounds substituted in position 3 with a $(C_1\text{-}C_6)$alkyl or $(C_2\text{-}C_6)$alkenyl group, to a composition for oxidation dyeing of the keratin fibres containing same, to a process for preparing said 1-hexyl-1H-pyrazole-4,5-diamine derivatives, to reaction intermediates, to an oxidation dyeing process using the composition, to the use of said 1-hexyl-1H-pyrazole-4,5-diamine derivatives for oxidation dyeing of keratin fibres, and also to a kit.

It is known practice to dye keratin fibres, and in particular human hair, with dye compositions containing oxidation dye precursors, which are generally known as oxidation bases. These oxidation bases are colourless or weakly coloured compounds which, when combined with oxidizing products, may give rise to coloured compounds and dyes via a process of oxidative condensation. These oxidation bases are generally ortho- or para-phenylenediamines, ortho- or para-aminophenols, or heterocyclic compounds such as pyrazole or pyrazolo pyrimidine derivatives.

It is also known that the shades obtained with these oxidation bases may be varied by combining them with colour modifiers, also known as couplers, the latter being chosen in particular from aromatic meta-diamines, meta-aminophenols, meta-diphenols and certain heterocyclic compounds.

The variety of molecules used as oxidation bases and couplers allows a wide range of colours to be obtained.

The "permanent" colouration obtained by means of these oxidation dyes should moreover satisfy a certain number of requirements. Thus, it should have no toxicological drawbacks, it should allow shades to be obtained in the desired intensity, and it should show good resistance to external agents (light, bad weather, washing, perspiration and rubbing).

The dyes should also allow grey hair to be covered and, finally, they should be as unselective as possible, i.e. they should allow the smallest possible differences in colour to be produced along the same keratin fibre, which in fact may be differently sensitized (that is to say damaged) between its end and its root. They must also have good chemical stability in formulations. They must have a good toxicological profile.

Furthermore, for a certain number of applications, dyes are sought which give chromatic and/or intense shades on the hair.

It is already known, for example in patent application EP 375 977, to use 4,5-diaminopyrazole derivatives in oxidation dyeing for dyeing keratin fibres. Compositions for oxidation dyeing comprising diaminopyrazole derivatives and couplers of the meta-phenylenediamine, meta-aminophenol or benzoxazine type are also known in patent applications EP 873 109, EP 871 426 and EP 692 245.

In addition, a series of patent applications describes the use of 1-hexyl-4,5-diaminopyrazole oxidation bases in the oxidation dyeing of the hair (WO 2013/122989, WO 2013/122990, US 20120210519, US 20120210520, US 20120210521, US 20120210522, US 20120210524, US 20120210525, and US 20120210526).

However, these compositions do not make it possible to meet all the requirements above, in particular in terms of resistance to washing and/or to light.

The aim of the present invention is to develop novel compounds and dye compositions containing them which make it possible to obtain colours of broad scope and do not have the drawbacks of the prior art dyes. In particular, the aim of the invention is to develop powerful dyes, particularly chromatic and bright dyes, that are not very selective and have excellent properties of resistance to the various attacks that keratin fibres may be subjected to, in particular with respect to light and/or to washing.

To this effect, a subject of the present invention is novel 1-hexyl-4,5-diaminopyrazole derivative compounds of formula (I) below:

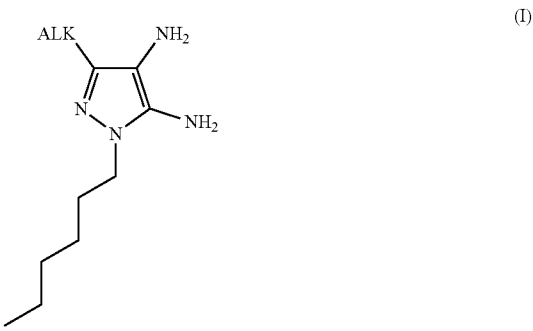

and also the addition salts thereof with organic or mineral acids, the tautomers thereof, and the solvates thereof such as hydrates; in which formula (I) ALK represents a linear or branched $(C_1\text{-}C_6)$alkyl or $(C_2\text{-}C_6)$alkenyl group, preferably $(C_1\text{-}C_4)$alkyl such as methyl.

A subject of the invention is also a composition for oxidation dyeing of keratin fibres, and in particular human keratin fibres such as the hair, characterized in that it contains, in a medium suitable for dyeing, as oxidation base at least one 1-hexyl-4,5-diaminopyrazole derivative of formula (I) as defined above, or an addition salt thereof with an acid, the tautomers thereof and the solvates thereof such as hydrates.

A subject of the invention is also a process for oxidation dyeing of keratin fibres using such a composition and the use of the 1-hexyl-4,5-diaminopyrazole derivatives of formula (I) as defined above, for dyeing keratin fibres, in particular human keratin fibres such as the hair.

A subject of the invention is also a process for preparing the 1-hexyl-4,5-diaminopyrazole derivatives of formula (I) as defined above and the reaction intermediates (4) and (4') as defined hereinafter.

As previously indicated, the dyes obtained from the oxidation dyeing composition in accordance with the invention are powerful, particularly bright and chromatic. They also have excellent properties of resistance with respect to the action of the various external agents (light, bad weather, washing, perspiration, rubbing), in particular with respect to successive shampooing operations and light.

In the context of the present invention, unless otherwise indicated:

the term "alkyl" is intended to mean a linear or branched radical containing from 1 to 6 carbon atoms, in particular from 1 to 4 carbon atoms, for example methyl, ethyl, n-propyl, isopropyl, butyl, n-pentyl, n-hexyl, preferably methyl;

the term "alkenyl" is intended to mean a radical comprising from 2 to 6 carbon atoms, preferably from 2 to 4 carbon atoms, and containing at least one double bond, preferably between 1 and 3 double bonds, which may be conjugated or non-conjugated, such as ethylenyl;

the term "organic or mineral acid salt" is intended to mean cosmetically acceptable salts, more particularly salts derived i) from mineral acids and from halogenated acids such as the salts of hydrochloric acid HCl, hydrobromic acid HBr, sulfuric acid $H_2SO_4$, ii) from ($C_1$-$C_6$)alkylsulfonic acids: Alk-S(O)$_2$OH such as methanesulfonic acid and ethanesulfonic acid; iii) from arylsulfonic acids: Ar—S(O)$_2$OH with Ar representing an aryl group, in particular phenyl group, such as salts derived from benzenesulfonic acid and toluenesulfonic acid; iv) from (poly)(hydroxy)($C_1$-$C_6$)alkylcarboxylic acids such as the salts of citric acid; of succinic acid; of tartaric acid; of lactic acid, x) from ($C_1$-$C_6$)alkoxysulfinic acids: Alk-O—S(O)OH such as methoxysulfinic acid and ethoxysulfinic acid; iv) from aryloxysulfinic acids such as tolueneoxysulfinic acid and phenoxysulfinic acid; vi) from phosphorus-based acids such as phosphoric acid $H_3PO_4$; v) from ($C_1$-$C_6$)alkylcarboxylic acids such as acetic acid $CH_3C(O)OH$; xiv) from triflic acid $CF_3SO_3H$; and vii) from tetrafluoroboric acid $HBF_4$;

the term "anionic counterion" is intended to mean an anion or an anionic group derived from an organic or mineral acid salt which counterbalances the cationic charge of the compound; more particularly, the anionic counterion is chosen from: i) halides such as chloride or bromide; ii) nitrates; iii) sulfonates, including $C_1$-$C_6$ alkylsulfonates: Alk-S(O)$_2$O$^-$ such as methanesulfonate or mesylate and ethanesulfonate; iv) arylsulfonates: Ar—S(O)$_2$O$^-$ such as benzenesulfonate and toluenesulfonate or tosylate; v) citrate; vi) succinate; vii) tartrate; viii) lactate; ix) alkyl sulfates: Alk-O—S(O)O$^-$ such as methyl sulfate and ethyl sulfate; x) aryl sulfates: Ar—O—S(O)O$^-$ such as benzene sulfate and toluene sulfate; xi) alkoxy sulfates: Alk-O—S(O)$_2$O$^-$ such as methoxy sulfate and ethoxy sulfate; xii) aryloxy sulfates: Ar—O—S(O)$_2$O$^-$, xiii) phosphates O=P(OH)$_2$—O$^-$, O=P(O$^-$)$_2$—OH O=P(O$^-$)$_3$, HO—[P(O)(O$^-$)]$_w$—P(O)(O$^-$)$_2$ with w being an integer; xiv) acetate; xv) triflate; and xvi) borates such as tetrafluoroborate, xvii) disulfate (O=)$_2$S(O$^-$)$_2$ or $SO_4^{2-}$ and monosulfate $HSO_4^-$;

the anionic counterion, derived from an organic or mineral acid salt, ensures the electrical neutrality of the molecule; thus, it is understood that when the anion comprises several anionic charges, then the same anion may serve for the electrical neutrality of several cationic groups in the same molecule or else may serve for the electrical neutrality of several molecules; for example, a compound which contains two cationic charges may contain either two "singly charged" anionic counterions or contains one "doubly charged" anionic counterion such as (O=)$_2$S(O$^-$)$_2$ or O=P(O$^-$)$_2$—OH;

an "aryl" radical represents a monocyclic or fused or non-fused polycyclic carbon-based group, comprising from 6 to 22 carbon atoms, at least one ring of which is aromatic; in particular, the aryl radical is a phenyl, biphenyl, naphthyl, indenyl, anthracenyl or tetrahydronaphthyl, preferably phenyl;

a "heteroaryl radical" represents an optionally cationic, 5- to 22-membered, monocyclic or fused or non-fused polycyclic group, comprising from 1 to 6 heteroatoms chosen from nitrogen, oxygen and sulfur, at least one ring of which is aromatic; preferentially, a heteroaryl radical is chosen from acridinyl, benzimidazolyl, benzobistriazolyl, benzopyrazolyl, benzopyridazinyl, benzoquinolyl, benzothiazolyl, benzotriazolyl, benzoxazolyl, pyridinyl, tetrazolyl, dihydrothiazolyl, imidazopyridinyl, imidazolyl, indolyl, isoquinolyl, naphthoimidazolyl, naphthoxazolyl, naphthopyrazolyl, oxadiazolyl, oxazolyl, oxazolopyridyl, phenazinyl, phenoxazolyl, pyrazinyl, pyrazolyl, pyrilyl, pyrazoyltriazyl, pyridyl, pyridinoimidazolyl, pyrrolyl, quinolyl, tetrazolyl, thiadiazolyl, thiazolyl, thiazolopyridinyl, thiazoylimidazolyl, thiopyrylyl, triazolyl, xanthylyl and the ammonium salt thereof;

the "aryl" or "heteroaryl" radicals or the aryl or heteroaryl part of a radical may be substituted with at least one substituent borne by a carbon atom, chosen from:

a $C_1$-$C_6$ alkyl radical optionally substituted with one or more radicals chosen from the radicals hydroxyl, $C_1$-$C_2$ alkoxy, $C_2$-$C_4$ (poly)hydroxyalkoxy, acylamino, amino substituted with two identical or different $C_1$-$C_4$ alkyl radicals which optionally bear at least one hydroxyl group or it being possible for the two radicals to form, with the nitrogen atom to which they are attached, a saturated or unsaturated and optionally substituted 5- to 7-membered and preferably 5- or 6-membered heterocycle optionally comprising another nitrogen or non-nitrogen heteroatom;

a halogen atom;

a hydroxyl group;

a $C_1$-$C_2$ alkoxy radical;

a $C_2$-$C_4$ (poly)hydroxyalkoxy radical;

an amino radical;

a 5- or 6-membered heterocycloalkyl radical;

a 5- or 6-membered heteroaryl radical, optionally substituted with a ($C_1$-$C_4$)alkyl radical, preferentially methyl;

an amino radical substituted with one or two identical or different $C_1$-$C_6$ alkyl radicals, optionally bearing at least:
  i) one hydroxyl group,
  ii) one amino group optionally substituted with one or two optionally substituted $C_1$-$C_3$ alkyl radicals, said alkyl radicals possibly forming with the nitrogen atom to which they are attached a saturated or unsaturated, optionally substituted 5- to 7-membered heterocycle, optionally comprising at least one other nitrogen or non-nitrogen heteroatom,
  iii) one quaternary ammonium group —N$^+$R'R''R''', M$^-$ for which R', R'' and R''', which may be identical or different, represent a hydrogen atom or a $C_1$-$C_4$ alkyl group; and M$^-$ represents the counterion of the organic or mineral acid or of the corresponding halide;

iv) or one optionally cationic 5- or 6-membered heteroaryl radical, preferentially imidazolium, optionally substituted with a ($C_1$-$C_4$)alkyl radical, preferentially methyl;

an acylamino radical (—NR—C(O)—R') in which the R radical is a hydrogen atom or a $C_1$-$C_4$ alkyl radical optionally bearing at least one hydroxyl group and the R' radical is a $C_1$-$C_2$ alkyl radical;

a carbamoyl radical (($R)_2$N—C(O)—) in which the R radicals, which may be identical or different, represent a hydrogen atom or a $C_1$-$C_4$ alkyl radical optionally bearing at least one hydroxyl group;

an alkylsulfonylamino radical (R'—S(O)$_2$—N(R)—) in which the R radical represents a hydrogen atom or a $C_1$-$C_4$ alkyl radical optionally bearing at least one hydroxyl group and the R' radical represents a $C_1$-$C_4$ alkyl radical or a phenyl radical; an aminosulfonyl radical (($R)_2$N—S(O)$_2$—) in which the R radicals, which may be identical or different, represent a hydrogen atom or a $C_1$-$C_4$ alkyl radical optionally bearing at least one hydroxyl group;

a carboxylic radical in acid or salified form (preferably with an alkali metal or a substituted or unsubstituted ammonium);

a cyano group;

a nitro or nitroso group;

a polyhaloalkyl group, preferentially trifluoromethyl.

The expression "at least one" is equivalent to the expression "one or more".

The keratin fibres treated via the process or those which are used according to the invention are in particular human keratin fibres and preferably the hair.

According to one particular embodiment of the invention, ALK represents a ($C_1$-$C_4$)alkyl group such as methyl, ethyl or n-propyl. Preferentially, the compound(s) of the invention are such that ALK represents a methyl group.

More particularly, the compound(s) of the invention are chosen from the compounds of formula (I') below:

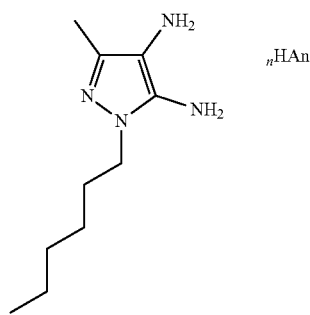

and also the tautomers thereof and the solvates thereof such as hydrates; in which formula (I'):

HAn represents an organic or mineral acid;

An represents the anionic counterion of said organic or mineral acid; it preferably represents an anionic counterion chosen from sulfate, halide such as hydrochloride or hydrobromide, acetate, citrate, tartrate, tosylate, and mesylate, methanesulfonate; more preferentially, An represents a sulfate, hydrochloride, acetate or methanesulfonate group; even more preferentially a sulfate or hydrochloride group;

n represents a number which may or may not be an integer, inclusively between 0.5 and 4; in particular, n is 0.5, 1 or 2;

it being understood that, when n is greater than or equal to 2, then An may be identical to or different from one another.

According to one particular embodiment, the dye(s) of formula (I) or (I') are in a form salified with n organic or mineral acids $_n$HAn, with n and HAn as defined for (I') and of which the acid(s) are chosen from sulfonic acids such as methanesulfonic acid, para-toluenesulfonic acid, sulfuric acid, halogenated acids such as hydrochloric and hydrobromic acid, and (poly)(hydroxy)($C_1$-$C_6$)alkylcarboxylic acids such as acetic acid, citric acid or tartaric acid. More preferentially, An represents a sulfate, hydrochloride, acetate or methanesulfonate group; even more preferentially, sulfate and hydrochloride.

The present invention relates to the salified 1-hexyl-3-methyl-1H-pyrazole-4,5-diamine compound, in particular in hemisulfate or sulfate form, and also to the compositions containing it for oxidation dyeing of keratin fibres and in particular of human keratin fibres.

According to one preferred embodiment, the dye(s) of formula (I) or (I') are chosen from those of formula (I") and also the solvates thereof such as hydrates:

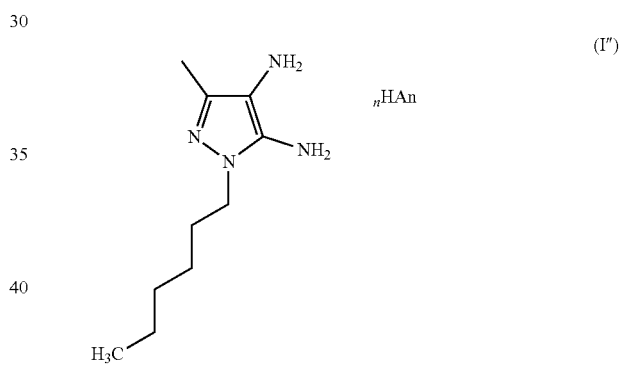

in which formula (I") HAn is as defined previously, and n represents a number, which may or may not be an integer, inclusively between 0.5 and 2; in particular n is 0.5, 1 or 2.

Preferably, An is an anionic counterion chosen from sulfate, hydrochloride, tartrate, acetate, hydrobromide, tosylate, mesylate, methanesulfonate and citrate.

Preferentially, the compounds of the invention are such that An is chosen from sulfate, hydrochloride, acetate and methanesulfonate, more preferentially An is chosen from sulfate, hydrochloride and methanesulfonate; even more preferentially sulfate and hydrochloride. Specifically, n HAn represents 0.5 $H_2SO_4$, 1 $H_2SO_4$, 2 HCl.

Process for Preparing the Compounds of Formula (I) or (I')

The compound(s) of formula (I) or (I') as defined previously are synthesized by conventional methods known to those skilled in the art.

The compound of structure (I) can be obtained for example via the synthesis process according to Scheme 1 below:

Scheme 1

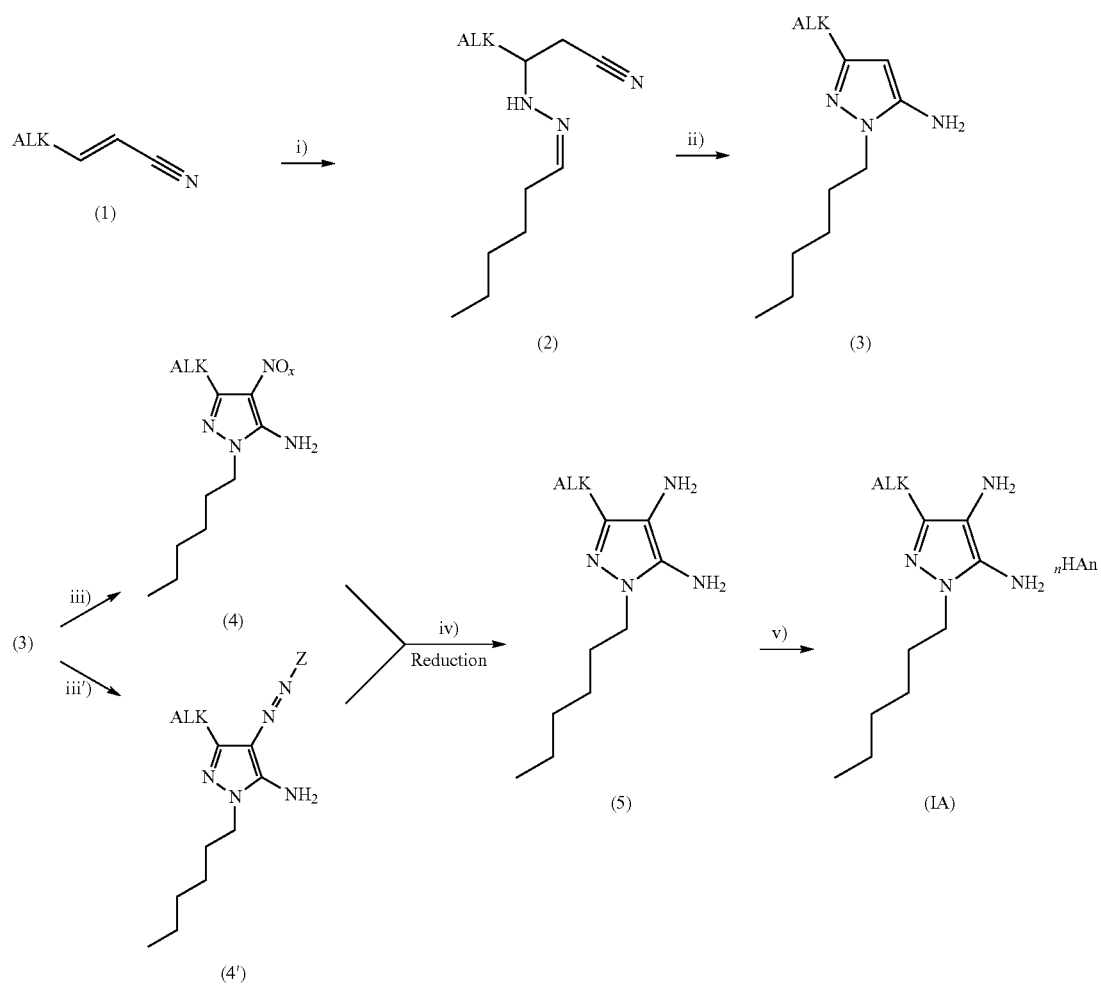

in which compounds 1 to 4, 4' and 5 and (IA) ALK are as defined for the compounds of formula (I) as defined previously, preferably ALK represents a $(C_1-C_4)$alkyl group such as methyl, An and n being as defined previously, x is 1 or 2, and Z representing an optionally substituted (hetero)aryl group such as optionally substituted phenyl;

which process consists in reacting:

during step i), a nitrile derivative ALK-CH=CH—CN (1) with hydrazine so as to give, after a nucleophilic reaction of the hydrazine with (1) of Michael 1,2 type, then addition of n-hexanal $CH_3—(CH_2)_4—C(O)H$, preferably at low temperature such as 0° C. and under an inert atmosphere, the compound of formula (2); then during step ii), the compound (2) with an alkaline agent which is preferably sterically hindered, in particular chosen from alkali metal and alkaline-earth metal salt $(C_3-C_{10})$alkanolates in which the alkyl part is branched or sterically hindered, such as alkali metal, alkaline-earth metal or ammonium tert-butoxides, preferably sodium or potassium tert-butoxides, preferably under an inert atmosphere in an organic, preferably polar protics, solvent such as a $(C_3-C_{10})$alkanol in which the alkyl part is linear or branched, such as tert-butanol, so as to give, after intramolecular cyclization, the 1-hexyl-5-aminopyrazolone derivative (3);

during step iii), the compound (3) is nitrated, in particular in a polar protic solvent such as ethanol and at low temperature such as 0° C. by the addition of a $(C_1-C_6)$ alkylnitrile, such as isopentyl nitrile, followed by the addition of a mineral acid, which is preferably halogenated, such as hydrochloric acid, at low temperature, preferably at 0° C., then aqueous ammonia is added, in particular at a pH above 11, optionally followed by an extraction preferably with water/halomethane such as dichloromethane, optionally followed by filtration so as to give the nitr(os)o compound (4); or else during step iii'), the compound (3) undergoes a treatment with a diazonium salt Z—NN$^+$Q$^-$ with Q$^-$ representing an anionic counterion and Z representing an optionally substituted aryl or heteroaryl group such as phenyl, in particular in a polar or polar protic solvent such as water, or a $(C_3-C_{10})$alkanol such as ethanol, preferably at a temperature of between −5° C. and 10° C., the azo coupling reaction is preferably followed by thin layer chromatography (TLC); the medium is preferably brought back to neutral pH, the solid precipitate is recovered by filtration so as to give the azo compound (4'); according to one variant, the solid can be extracted with an organic solvent, in particular a non-protic polar solvent such as ethyl acetate or a halogenated solvent such as dichloromethane, to give the azo compound (4');

during step iv), the compound (4) or (4') is reduced, preferably under an inert atmosphere, in particular in a polar protic solvent such as ethanol and with a catalyst such as Ni or Pd and preferably in the presence of hydrazine, so as to give the compound (5) belonging to the compound of formula (I) as defined previously; then during step v), the compound (5) can optionally be salified using an organic or mineral acid, as defined previously, preferably using a mineral acid such as hydrochloric acid or sulfuric acid, in particular a sulfur-comprising acid such as sulfuric acid, to give the compound (IA) belonging to the compound of formula (I) as defined previously.

According to particular embodiments, the compounds (2) to (5) and (IA) are obtained in the following way:

The compounds (2) can be obtained by conventional methods known to those skilled in the art from compounds that are readily accessible either by syntheses or starting from commercial products.

For example, the compounds (2) can be obtained by reacting i) hydrazine or the salts or hydrates thereof, preferably at low temperature, in particular between −5° C. and 5° C., such as 0° C., in a solvent, preferably a polar protic solvent such as $(C_1-C_6)$alkanols, in particular 1-propanol, with ii) the compounds (1) ALK-CH=CH—CN.

The compounds (3) can be obtained by reacting i) a sterically hindered organic base, preferably a $(C_3-C_6)$alkanolate of an alkali metal, alkaline-earth metal or ammonium salt, such as potassium tert-butoxide preferably under an inert atmosphere, and in a solvent, in particular a polar protic solvent, preferably a $(C_3-C_6)$alkanol such as tert-butanol, with ii) the compounds (2), followed by heating of the mixture, in particular between 40 and 60° C., preferably for 1 to 30 minutes, then at reflux of the solvent, in particular for 1 hour to 5 hours. The reaction can be monitored by chromatography, for example by thin layer chromatography, in particular on silica with, for example, a heptane/ethyl acetate eluent. At the end of the reaction, the medium is returned to ambient temperature, followed by extraction(s) with water and a water-immiscible solvent, such as halogenated solvents, for instance dichloromethane, aromatic solvents such as toluene, or diethyl ether, the organic phase is recovered, optionally dried, for example with magnesium sulfate, and filtered, and then the solvent is evaporated off, preferably under reduced pressure, to give the compounds (3).

The compounds (4) can be obtained by reacting a) the compounds 3, in a solvent, preferably a polar protic solvent such as ethanol, in particular at low temperature at a temperature between −5° C. and 5° C., in the presence of a $(C_1-C_6)$alkylnitrile such as isopentylnitrile, with an acid, preferably a mineral acid, such as hydrochloric acid, which can b) then undergo extraction with an ethereal organic solvent such as isopropyl ether, followed c) by the addition of an alkaline agent so as to obtain a basic pH, preferably of between 9 and 12, such as 11, optionally followed by extraction with a halogenated solvent such as dichloromethane. The organic phases are then recovered and optionally dried with a drying agent such as magnesium sulfate, and then filtered to give the compounds (4).

Another subject of the invention is the synthesis intermediate compounds (4) and (4') and also the organic or mineral acid or base salts thereof, the optical and geometric isomers and the tautomers thereof, and the solvates thereof such as hydrates:

(4)

(4')

in which compounds (4) and (4'), ALK is as defined for the compounds of formula (I) defined previously, preferably ALK represents a $(C_1-C_4)$alkyl group such as methyl, An and n being as defined previously, x is 1 or 2, and Z representing an optionally substituted aryl or optionally substituted heteroaryl group such as phenyl, it being understood that the compound (4) is different from (A) and the compound (4') is different from (B), from (C) and from (D):

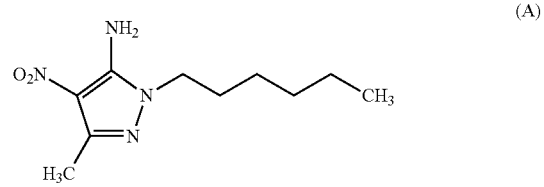

(A)

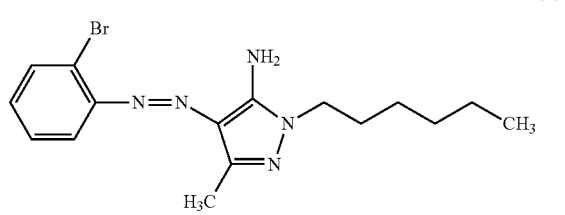

(B)

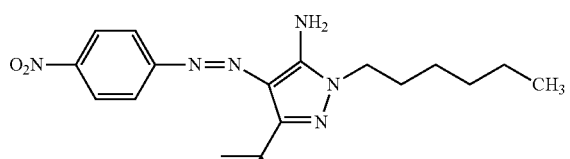

(C)

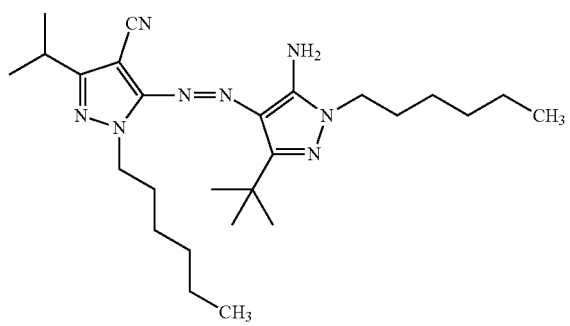

(D)

Another subject of the invention is a composition for oxidation dyeing of keratin fibres, and in particular human keratin fibres such as the hair, characterized in that it contains, in a medium suitable for dyeing, as oxidation base, i) at least one compound of formula (I) or an addition salt thereof with an acid, (I'), or (I") as defined above, the tautomers thereof and the solvates thereof such as hydrates.

The composition according to the invention generally contains from 0.001% to 10% by weight, preferably from 0.05% to 6% by weight, and more preferentially from 0.1% to 3% by weight, of at least one compound of formula (I), (I') or (I") and also the addition salts thereof with organic or mineral acids, the tautomers thereof, and the solvates thereof such as hydrates.

The composition in accordance with the invention can contain, in addition to i) the compound(s) of formula (I), (I'), or (I") as defined previously, ii) one or more additional oxidation base(s) different from the compound(s) of formula (I), (I'), or (I"), which can be chosen from the oxidation bases conventionally used in oxidation dyeing. Particularly, the additional oxidation base(s) is (are) chosen from para-phenylenediamines, bis-phenylalkylenediamines, para-aminophenols, ortho-aminophenols and heterocyclic bases different from the compound(s) of formula (I), (I'), or (I") as defined previously.

According to one particular embodiment, the additional oxidation base(s) is (are) chosen from para-phenylenediamines, more particularly chosen from para-phenylenediamine, para-toluenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(p-hydroxyethyl)-para-phenylenediamine, 4-N,N-bis(p-hydroxyethyl) amino-2-methylaniline, 4-N,N-bis(p-hydroxyethyl)amino-2-chloroaniline, 2-p-hydroxyethyl-para-phenylenediamine, 2-methoxymethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene and 3-hydroxy-1-(4'-aminophenyl)pyrrolidine, and the corresponding addition salts with an acid.

Among the para-phenylenediamines mentioned above, para-phenylenediamine, para-toluenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine, and the corresponding addition salts with an acid, are particularly preferred.

According to one particular embodiment, the additional oxidation base(s) is (are) chosen from bis(phenyl)alkylenediamines, more particularly chosen from N,N'-bis(β-hydroxyethyl)-N,N'-bis(4'-aminophenyl)-1,3-diaminopropanol, N,N'-bis(β-hydroxyethyl)-N,N'-bis(4'-aminophenyl) ethylenediamine, N,N'-bis(4-aminophenyl) tetramethylenediamine, N,N'-bis(β-hydroxyethyl)-N,N'-bis (4-aminophenyl)tetramethylenediamine, N,N'-bis(4-methylaminophenyl)tetramethylenediamine, N,N'-bis (ethyl)-N,N'-bis(4'-amino-3'-methylphenyl)ethylenediamine and 1,8-bis(2,5-diaminophenoxy)-3,6-dioxaoctane, and the corresponding addition salts.

According to one particular embodiment, the additional oxidation base(s) is (are) chosen from para-aminophenols, more particularly chosen from para-aminophenol, 4-amino-3-methylphenol, 4-amino-3-fluorophenol, 4-amino-3-chlorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethyl-aminomethyl)phenol and 4-amino-2-fluorophenol, and the corresponding addition salts with an acid.

According to one particular embodiment, the additional oxidation base(s) is (are) chosen from ortho-aminophenols, more particularly chosen from 2-aminophenol, 2-amino-5-methylphenol, 2-amino-6-methylphenol and 5-acetamido-2-aminophenol and the corresponding addition salts.

According to one particular embodiment, the additional oxidation base(s) is (are) chosen from heterocyclic bases, more particularly those derived from pyridine, from pyrimidine and from pyrazole that are different from the compound(s) of formula (I), (I'), or (I") as defined previously.

Among the pyridine derivatives that may be mentioned are the compounds described, for example, in patents GB 1 026 978 and GB 1 153 196, for example 2,5-diaminopyridine, 2-(4-methoxyphenyl)amino-3-aminopyridine and 3,4-diaminopyridine, and the corresponding addition salts.

Other pyridine oxidation bases that are useful in the present invention are the 3-aminopyrazolo[1,5-a]pyridine oxidation bases or the corresponding addition salts described, for example, in patent application FR 2 801 308. Examples that may be mentioned include pyrazolo[1,5-a] pyrid-3-ylamine, 2-acetylaminopyrazolo[1,5-a]pyrid-3-ylamine, 2-(morpholin-4-yl)pyrazolo[1,5-a]pyrid-3-ylamine, 3-aminopyrazolo[1,5-a]pyridine-2-carboxylic acid, 2-methoxypyrazolo[1,5-a]pyrid-3-ylamine, (3-aminopyrazolo[1,5-a]pyrid-7-yl)methanol, 2-(3-aminopyrazolo[1,5-a]pyrid-5-yl)ethanol, 2-(3-aminopyrazolo[1,5-a]pyrid-7-yl)ethanol, (3-aminopyrazolo[1,5-a]pyrid-2-yl)methanol, 3,6-diaminopyrazolo[1,5-a]pyridine, 3,4-diaminopyrazolo[1,5-a]pyridine, pyrazolo[1,5-a]pyridine-3,7-diamine, 7-(morpholin-4-yl)pyrazolo[1,5-a]pyrid-3-ylamine, pyrazolo[1,5-a]pyridine-3,5-diamine, 5-(morpholin-4-yl)pyrazolo[1,5-a]pyrid-3-ylamine, 2-[(3-aminopyrazolo[1,5-a]pyrid-5-yl)(2-hydroxyethyl)amino]ethanol, 2-[(3-aminopyrazolo[1,5-a]pyrid-7-yl)(2-hydroxyethyl)amino]ethanol, 3-aminopyrazolo[1,5-a]pyridin-5-ol, 3-aminopyrazolo[1,5-a]pyridin-4-ol, 3-aminopyrazolo[1,5-a]pyridin-6-ol, 3-aminopyrazolo[1,5-a]pyridin-7-ol, 2-β-hydroxyethoxy-3-aminopyrazolo[1,5-a]pyridine and 2-(4-dimethylpiperazinium-1-yl)-3-aminopyrazolo[1,5-a]pyridine, and the corresponding addition salts.

More particularly, the oxidation bases that are useful in the present invention are chosen from 3-aminopyrazolo[1,5-a]pyridines and are preferably substituted on carbon atom 2 with:

a) a (di)($C_1$-$C_6$)(alkyl)amino group, said alkyl group possibly being substituted with at least one hydroxyl, amino or imidazolium group;

b) an optionally cationic 5- to 7-membered heterocycloalkyl group comprising from 1 to 3 heteroatoms, optionally substituted with one or more ($C_1$-$C_6$)alkyl groups such as a di($C_1$-$C_4$)alkylpiperazinium group; or c) a ($C_1$-$C_6$)alkoxy group optionally substituted with one or more hydroxyl groups, such as a p-hydroxyalkoxy group, and the corresponding addition salts.

Among the pyrimidine derivatives that may be mentioned are the compounds described, for example, in patents DE 2359399; JP 88-169571; JP 05-63124; EP 0770375 or patent application WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine and the addition salts thereof and the tautomeric forms thereof, when a tautomeric equilibrium exists.

Among the pyrazole derivatives that may be mentioned are the compounds described in patents DE 3843892 and DE 4133957 and patent applications WO 94/08969, WO 94/08970, FR-A-2 733 749 and DE 195 43 988, for instance 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole and 3,5-diamino-4-(β-hydroxyethyl)amino-1-methylpyrazole, and the corresponding addition salts. Use may also be made of 4,5-diamino-1-(β-methoxyethyl)pyrazole.

A 4,5-diaminopyrazole will preferably be used and even more preferentially 4,5-diamino-1-(β-hydroxyethyl)pyrazole and/or a corresponding salt.

The pyrazole derivatives that may also be mentioned include diamino-N,N-dihydropyrazolopyrazolones and in particular those described in patent application FR-A-2 886 136, such as the following compounds and the corresponding addition salts: 2,3-diamino-6,7-dihydro-1H,5H-pyrazolo[1,2-a]pyrazol-1-one, 2-amino-3-ethylamino-6,7-dihydro-1H,5H-pyrazolo[1,2-a]pyrazol-1-one, 2-amino-3-isopropylamino-6,7-dihydro-1H,5H-pyrazolo[1,2-a]pyrazol-1-one, 2-amino-3-(pyrrolidin-1-yl)-6,7-dihydro-1H,5H-pyrazolo[1,2-a]pyrazol-1-one, 4,5-diamino-1,2-dimethyl-1,2-dihydropyrazol-3-one, 4,5-diamino-1,2-diethyl-1,2-dihydropyrazol-3-one, 4,5-diamino-1,2-bis(2-hydroxyethyl)-1,2-dihydropyrazol-3-one, 2-amino-3-(2-hydroxyethyl)amino-6,7-dihydro-1H,5H-pyrazolo[1,2-a]pyrazol-1-one, 2-amino-3-dimethylamino-6,7-dihydro-1H,5H-pyrazolo[1,2-a]pyrazol-1-one, 2,3-diamino-5,6,7,8-tetrahydro-1H,6H-pyridazino[1,2-a]pyrazol-1-one, 4-amino-1,2-diethyl-5-(pyrrolidin-1-yl)-1,2-dihydropyrazol-3-one, 4-amino-5-(3-dimethylaminopyrrolidin-1-yl)-1,2-diethyl-1,2-dihydropyrazol-3-one and 2,3-diamino-6-hydroxy-6,7-dihydro-1H,5H-pyrazolo[1,2-a]pyrazol-1-one.

Use will preferably be made of 2,3-diamino-6,7-dihydro-1H,5H-pyrazolo[1,2-a]pyrazol-1-one and/or a corresponding salt.

Heterocyclic bases that will preferably be used include 4,5-diamino-1-(β-hydroxyethyl)pyrazole, 4,5-diamino-1-hexylpyrazole and/or 2,3-diamino-6,7-dihydro-1H,5H-pyrazolo[1,2-a]pyrazol-1-one and/or a corresponding salt.

The composition according to the invention may optionally comprise iii) one or more coupling agents advantageously chosen from those conventionally used in the dyeing of keratin fibres.

Among these coupling agents, mention may be made in particular of meta-phenylenediamines, meta-aminophenols, meta-diphenols, naphthalene-based coupling agents and heterocyclic coupling agents, and also the corresponding addition salts.

Mention may be made, for example, of 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene, 2,6-bis(β-hydroxyethylamino)toluene, 6-hydroxyindoline, 2,6-dihydroxy-4-methylpyridine, 1-H-3-methylpyrazol-5-one, 1-phenyl-3-methylpyrazol-5-one, 2,6-dimethylpyrazolo[1,5-b]-1,2,4-triazole, 2,6-dimethyl[3,2-c]-1,2,4-triazole and 6-methylpyrazolo[1,5-a]benzimidazole, 2-methyl-5-aminophenol, 5-N-(β-hydroxyethyl)amino-2-methylphenol, 3-aminophenol and 3-amino-2-chloro-6-methylphenol, the corresponding addition salts with an acid and the corresponding mixtures.

More particularly, the coupling agent(s) of the invention is (are) chosen from the compounds of formulae (II) and (II'):

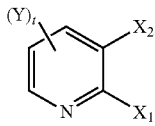
(II')

and also the organic or mineral acid or base salts thereof, and the solvates thereof such as hydrates;
in which formulae (II) and (II'):
- $X_1$ and $X_2$, which may be identical or different, represent a group chosen from hydroxyl, (di)($C_1$-$C_6$)(alkyl) amino and (di)hydroxy($C_1$-$C_6$)alkylamino;
- Y represents a hydrogen atom or ($C_1$-$C_6$)(hydroxy)alkyl, or else two adjacent substituents Y and $X_1$ and/or Y and $X_2$ form, together with the carbon atoms which bear them, an optionally substituted heterocyclic group, such as morpholinyl, piperazinyl, piperidinyl, preferably a hydrogen atom, ($C_1$-$C_6$)alkyl, or else two adjacent substituents Y and $X_1$ form, together with the carbon atoms which bear them, a morpholinyl group optionally substituted with a ($C_1$-$C_4$)alkyl group;
- p is 1, 2, 3 or 4;
- t is 1, 2 or 3;

it being understood that, when p or t is greater than or equal to 2, the Y groups are identical to or different from one another.

More particularly, the coupling agent(s) of the invention is (are) chosen from the compounds of formulae ($II_a$) and ($II'_a$):

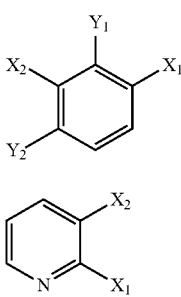

and also the organic or mineral acid or base salts thereof, and the solvates thereof such as hydrates;
in which formulae (IIa) and (II'a):
- $X_1$ and $X_2$ are as defined previously, preferably $X_1$ and/or $X_2$ represent(s) a hydroxyl, amino or (hydroxy)alkylamino group;
- $Y_1$ represents a hydrogen atom or a ($C_1$-$C_6$)alkyl group;
- $Y_2$ represents a hydrogen atom, or forms, with the substituent $Y_2$, an optionally substituted heterocycle, such as morpholinyl, piperazinyl or piperidinyl, preferably morpholinyl optionally substituted with a ($C_1$-$C_4$)alkyl group.

Preferably, the coupler(s) of the invention are chosen from: 2-methylresorcinol, 6-hydroxybenzomorpholine; 2-amino-3-hydroxypyridine; 2-({3-[(2-hydroxyethyl)amino]-2-methylphenyl}amino)ethanol and also the acid or base salts thereof and the solvates thereof such as hydrates.

In general, the addition salts of oxidation bases and couplers that may be used in the context of the invention are chosen in particular from the addition salts with an acid such as the hydrochlorides, hydrobromides, sulfates, citrates, succinates, tartrates, lactates, tosylates, benzenesulfonates, phosphates and acetates.

When they are present, the additional oxidation base(s) each advantageously represent from 0.001% to 10% by weight relative to the total weight of the composition, and preferably from 0.005% to 5% by weight relative to the total weight of the composition and of the ready-to-use composition.

The coupler(s), if it (they) are present, each advantageously represent(s) from 0.001% to 10% by weight relative to the total weight of the composition, and preferably from 0.005% to 5% by weight relative to the total weight of the composition and of the ready-to-use composition.

The composition according to the invention may optionally comprise iv) one or more synthetic or natural direct dyes chosen from anionic and non-ionic species, preferably cationic or non-ionic species, either as sole dyes or in addition to the oxidation dye(s).

Examples of suitable direct dyes that may be mentioned include azo direct dyes; (poly)methine dyes such as cyanines, hemicyanines and styryls; carbonyl dyes; azine dyes; nitro(hetero)aryl dyes; tri(hetero)arylmethane dyes; porphyrin dyes; phthalocyanine dyes and natural direct dyes, alone or in the form of mixtures.

The direct dyes are preferably cationic direct dyes. Mention may be made of the hydrazono cationic dyes of formulae (IIIa) and (III'a), the azo cationic dyes (IVa) and (IV'a) and the diazo cationic dyes (Va) below:

$$Het^+ \!-\! C(R^a) \!=\! N \!-\! N(R^b) \!-\! Ar, An^- \quad (IIIa)$$

$$Het^+ \!-\! N(R^a) \!=\! N \!-\! C(R^b) \!-\! Ar, An^- \quad (III'a)$$

$$Het^+ \!-\! N \!=\! N \!-\! Ar, An^- \quad (IVa)$$

$$Ar^+ \!-\! N \!=\! N \!-\! Ar'', An^- \quad \text{and} \quad (IV'a)$$

$$Het^+ \!-\! N \!=\! N \!-\! Ar' \!-\! N \!=\! N \!-\! Ar, An^- \quad (Va)$$

in which formulae (IIIa), (III'a), (IVa), (IV'a) and (Va):
- $Het^+$ represents a cationic heteroaryl radical, preferably bearing an endocyclic cationic charge, such as imidazolium, indolium or pyridinium, optionally substituted preferably with one or more ($C_1$-$C_8$)alkyl groups such as methyl;
- $Ar^+$ represents an aryl radical, such as phenyl or naphthyl, bearing an exocyclic cationic charge, preferably ammonium, particularly tri($C_1$-$C_8$)alkylammonium such as trimethylammonium;
- Ar represents an aryl group, in particular phenyl, which is optionally substituted, preferably with one or more electron-donating groups such as i) optionally substituted ($C_1$-$C_8$)alkyl, ii) optionally substituted ($C_1$-$C_8$) alkoxy, iii) (di)($C_1$-$C_8$)(alkyl)amino optionally substituted on the alkyl group(s) with a hydroxyl group, iv) aryl($C_1$-$C_8$)alkylamino, v) optionally substituted N—($C_1$-$C_8$)alkyl-N-aryl($C_1$-$C_8$)alkylamino or, as a variant, Ar represents a julolidine group;
- Ar' represents an optionally substituted divalent (hetero)arylene group such as phenylene, particularly para-phenylene, or naphthalene, which are optionally substituted, preferably with one or more ($C_1$-$C_8$)alkyl, hydroxyl or ($C_1$-$C_8$)alkoxy groups;

Ar" represents an optionally substituted (hetero)aryl group such as phenyl or pyrazolyl, which are optionally substituted, preferably with one or more $(C_1-C_8)$alkyl, hydroxyl, $(di)(C_1-C_8)(alkyl)$amino, $(C_1-C_8)$alkoxy or phenyl groups;

$R^a$ et $R^b$, which may be identical or different, represent a hydrogen atom or a $(C_1-C_8)$alkyl group, which is optionally substituted, preferably with a hydroxyl group;

or, as a variant, the substituent $R^a$ with a substituent of Het$^+$ and/or $R^b$ with a substituent of Ar and/or $R^a$ with $R^b$ form, together with the atoms that bear them, a (hetero)cycloalkyl;

particularly, $R^a$ and $R^b$ represent a hydrogen atom or a $(C_1-C_4)$alkyl group, which is optionally substituted with a hydroxyl group;

An$^-$ represents an anionic counterion, such as mesylate or halide.

Mention may be made in particular of azo and hydrazono cationic dyes bearing an endocyclic cationic charge of formulae (IIIa), (III'a) and (IVa) as defined previously, more particularly those of formulae (IIIa), (III'a) and (IVa) derived from the dyes described in patent applications WO 95/15144, WO 95/01772 and EP-714954.

Preferably, the cationic part is derived from the following derivatives:

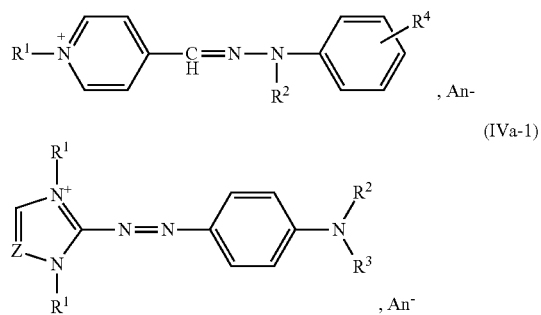

in which formulae (III-1) and (IV-1):

R' represents a $(C_1-C_4)$alkyl group such as methyl;

$R^2$ and $R^3$, which may be identical or different, represent a hydrogen atom or a $(C_1-C_4)$alkyl group, such as methyl; and $R^4$ represent a hydrogen atom or an electron-donating group such as an optionally substituted $(C_1-C_8)$alkyl group, an optionally substituted $(C_1-C_8)$alkoxy group, or a $(di)(C_1-C_8)(alkyl)$amino group optionally substituted on the alkyl group(s) with a hydroxyl group; in particular, $R^4$ represents a hydrogen atom, Z represents a CH group or a nitrogen atom, preferably CH, An$^-$ represents an anionic counterion, such as mesylate or halide.

In particular, the dye of formulae (IIIa-1) and (IVa-1) is chosen from Basic Red 51, Basic Yellow 87 and Basic Orange 31 or corresponding derivatives:

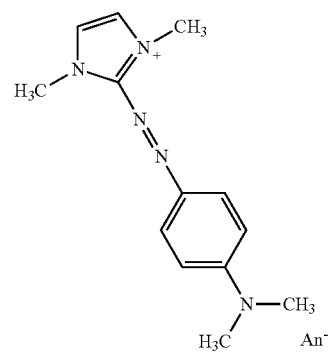

Basic Red 51

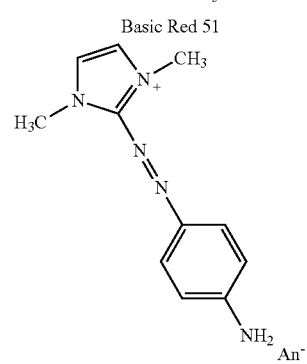

Basic Orange 31

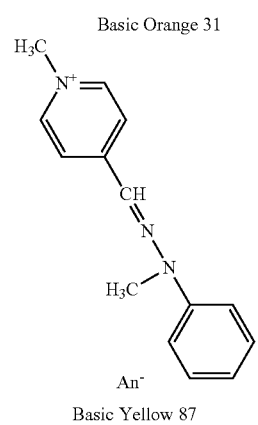

Basic Yellow 87

An$^-$ represents an anionic counterion, such as mesylate or halide.

Among the natural direct dyes that may be used according to the invention, mention may be made of hennotannic acid, juglone, alizarin, purpurin, carminic acid, kermesic acid, purpurogallin, protocatechaldehyde, indigo, isatin, curcumin, spinulosin, apigenidin and orcein. Extracts or decoctions containing these natural dyes and in particular henna-based poultices or extracts may also be used.

When they are present, the direct dye(s) iv) more particularly represent from 0.001% to 10% by weight and preferably from 0.005% to 5% by weight relative to the total weight of the composition.

The medium suitable for dyeing (or support) used according to the invention is constituted of water or of a mixture of water and at least one organic solvent chosen from $C_1-C_4$ lower alkanols, polyols and polyol ethers, aromatic alcohols, analogous products and mixtures thereof.

The dye composition in accordance with the invention may also contain various adjuvants conventionally used in hair dye compositions, such as anionic, cationic, non-ionic, amphoteric or zwitterionic surfactants or mixtures thereof, anionic, cationic, non-ionic, amphoteric or zwitterionic polymers or mixtures thereof, mineral or organic thickeners, and in particular anionic, cationic, non-ionic and amphoteric polymeric associative thickeners, antioxidants, penetrants, sequestrants, fragrances, buffers, dispersants, conditioning agents, for instance volatile or non-volatile, modified or unmodified silicones, film-forming agents, ceramides, preserving agents and opacifiers.

The pH of the dye composition in accordance with the invention is generally between 3 and 12 approximately and preferably between 5 and 11 approximately. It can be adjusted to the desired value by means of acidifying or basifying agents regularly used in the dyeing of keratin fibres or alternatively using conventional buffer systems.

Among the acidifying agents that may be mentioned, by way of example, are mineral or organic acids, for instance hydrochloric acid, orthophosphoric acid or sulfuric acid, carboxylic acids, for instance acetic acid, tartaric acid, citric acid and lactic acid, and sulfonic acids.

Among the basifying agents, examples that may be mentioned include aqueous ammonia, alkali metal carbonates, alkanolamines, such as mono-, di- and triethanolamines and derivatives thereof, sodium hydroxide, potassium hydroxide and the compounds of formula (V) below:

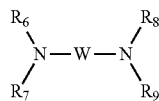
(V)

in which formula (V) W is a linear or branched $(C_1-C_6)$ alkylene group, in particular propylene, optionally substituted with one or more hydroxyl groups; $R_6$, $R_7$, $R_8$ et $R_9$, which may be identical or different, represent a hydrogen atom or a $C_1-C_4$ alkyl or $C_1-C_4$ hydroxyalkyl radical.

Needless to say, those person skilled in the art will take care to select this or these optional additional compound(s) such that the advantageous properties intrinsically associated with the oxidation dye composition in accordance with the invention are not, or are not substantially, adversely affected by the envisaged addition(s).

The dye composition according to the invention may be in various forms, such as in the form of liquids, creams or gels, or in any other form that is suitable for dyeing keratin fibres, and in particular human hair.

A subject of the invention is also a process for dyeing keratin fibres and in particular human keratin fibres such as the hair, using the dye composition as defined previously.

According to this process, at least one dye composition as defined previously is applied to the fibres for a period of time sufficient to develop the desired colouration, either in the air, or by means of an oxidizing agent. The dye composition can optionally contain oxidation catalysts, in order to accelerate the oxidation process.

According to a first embodiment of the process of the invention, at least one dye composition as defined previously is applied to the fibres, the colour being revealed at acid, neutral or alkaline pH by means of an oxidizing agent which is added to the dye composition just at the time of use or which is present in an oxidizing composition applied simultaneously or sequentially separately.

According to this second embodiment of the dyeing process of the invention, the dye composition described above is preferably mixed, at the time of use, with an oxidizing composition containing, in a medium suitable for dyeing, at least one oxidizing agent present in an amount sufficient to develop a colouration. The mixture obtained is subsequently applied to the keratin fibres and left on for 3 to 50 minutes, preferably 5 to 30 minutes, after which the fibres are rinsed, washed with shampoo, rinsed again and dried.

The oxidizing agent present in the oxidizing composition as defined above can be chosen from the oxidizing agents conventionally used for the oxidation dyeing of keratin fibres, and among which mention may be made of hydrogen peroxide, urea peroxide, alkali metal bromates, persalts such as perborates and persulfates, peracids, oxidase enzymes, including peroxydases, 2-electron oxidoreductases, such as uricases, and 4-electron oxygenases, such as laccases. Hydrogen peroxide is particularly preferred.

The pH of the oxidizing composition containing the oxidizing agent as defined above is such that, after mixing with the dye composition, the pH of the resulting composition applied to the keratin fibres preferably ranges between 3 and 12 and even more preferentially between 5 and 11. It is adjusted to the desired value by means of acidifying or basifying agents usually used in the dyeing of keratin fibres and as defined above.

The oxidizing composition as defined above may also contain various adjuvants conventionally used in compositions for dyeing the hair and as defined above.

The composition which is ultimately applied to the keratin fibres may be in various forms, such as in the form of liquids, creams or gels, or in any other form that is suitable for dyeing keratin fibres, and in particular human hair.

Another subject of the invention is the use of one or more compound(s) of formula (I), (I') or (I") as defined previously, optionally in the presence of additional oxidation base(s) as defined previously, and/or optionally in the presence of one or more coupler(s) as defined previously, and/or optionally in the presence of oxidizing agent(s) in particular as defined previously, for dyeing keratin fibres, in particular human keratin fibres such as the hair.

Preferentially, the use relates to the use of one or more compound(s) of formula (I), (I') or (I") as defined previously, in the presence of one or more coupler(s) as defined previously, and in the presence of oxidizing agent(s) in particular as defined previously, for dyeing keratin fibres, in particular human keratin fibres such as the hair.

Another subject of the invention is a multi-compartment dyeing device or dyeing "kit" or any other multi-compartment packaging system of which a first compartment contains the dye composition as defined above and a second compartment contains an oxidizing composition. These devices may be equipped with a means for dispensing the desired mixture on the hair, such as the devices described in patent FR-2 586 913 in the name of the Applicant.

EXAMPLES

Synthesis Example

Process 1: Via a Nitro or Nitroso Reaction Intermediate

Preparation of 3-[2-hexylidenehydrazinyl]butanenitrile: Compound 2

Synthesis scheme 1

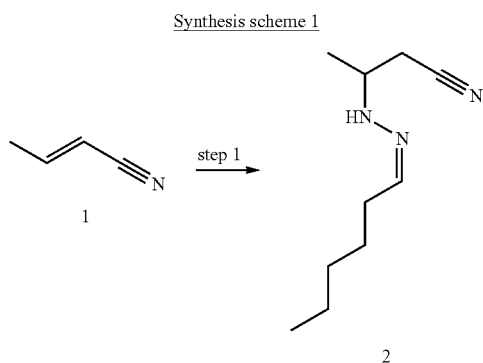

120 ml of 1-propanol and 42.6 g of hydrazine hydrate are charged, under nitrogen, to a three-necked reaction vessel equipped with magnetic stirring, a thermometer, a reflux condenser and a dropping funnel, and then, at 0° C., 60 g of crotonitrile 1 are run in dropwise. The stirring of the mixture obtained is maintained for 10 minutes at 0° C. and then for 1 hour at ambient temperature.

89.6 g of hexanal are then introduced dropwise and the stirring is continued for 20 minutes at ambient temperature before concentrating until a crude product 2 is obtained in the form of an orange oil (153.52 g). The product 2 thus obtained is used in the subsequent step without further purification.

The spectroscopic and spectrometric analyses agree with the structure of the expected compound 2.

Preparation of 1-hexyl-3-methyl-1H-pyrazol-5-amine: Compound 3

Synthesis scheme 2

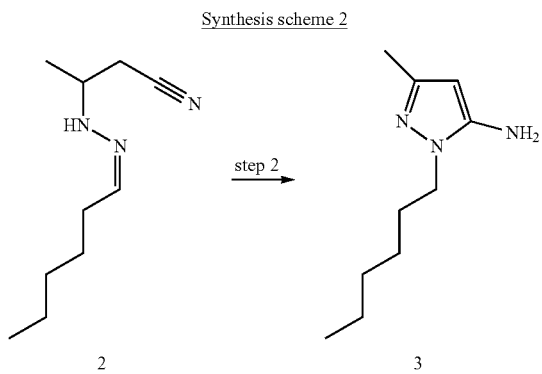

Introduced, under nitrogen, into a 2-litre three-necked reaction vessel equipped with mechanical stirring, a thermometer, a reflux condenser and a dropping funnel are tert-butanol (1.6 l), the crude compound 2 (153.52 g), and potassium tert-butoxide (95 g). The suspension obtained is brought to 50° C. for a few minutes and then to reflux for 3 h 30. The reaction is monitored by TLC analysis (6/4 heptane/ethyl acetate). At the end of the reaction, the suspension was cooled to ambient temperature and then poured into 750 ml of water. The resulting mixture was extracted twice with diethyl ether. The combined organic phases were washed with a 1N hydrochloric acid solution. The aqueous phase was added to a saturated solution of NaCl salt and then a concentrated sodium hydroxide solution was added to basic pH before extraction twice with diethyl ether. The organic phase was dried over magnesium sulfate, filtered and concentrated so as to give an orange solid corresponding to the compound 3 (6.6 g). The organic phase previously obtained was partially concentrated to 2/3 and ethyl ether was added thereto. Concentrated sodium hydroxide was added to the resulting aqueous phase until a basic pH was obtained, followed by extraction twice with diethyl ether. The various organic phases were combined, dried over magnesium sulfate, filtered and concentrated so as to give a second batch of compound 3 in the form of an orange solid (129.6 g). The product was used in the subsequent step without further purification. The spectroscopic and spectrometric analyses agree with the structure of the expected compound 3.

Preparation of 1-hexyl-3-methyl-4-nitroso-1H-pyrazol-5-amine: Compound 4

Synthesis scheme 3

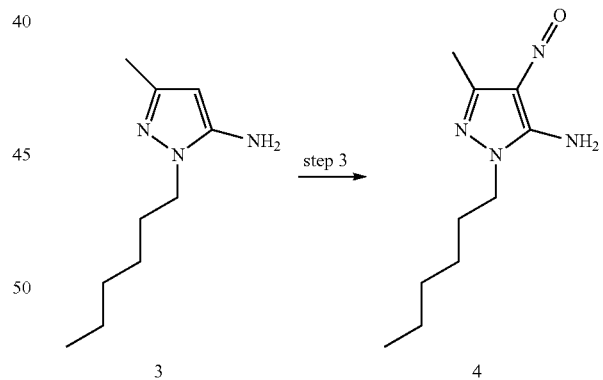

In a 1-litre three-necked reaction vessel, equipped with mechanical stirring, a thermometer, a reflux condenser and a dropping funnel, a solution of crude compound 3 (50 g) in 270 ml of ethanol was prepared and then, after cooling to 0° C. and with stirring, 49 ml of isopentyl nitrile were added dropwise.

The resulting solution was added dropwise to a solution of concentrated hydrochloric acid (27 ml) in dimethyl ether ethylene glycol (75 ml) precooled to 0° C. (exothermic reaction). The mixture obtained was kept stirring for 20 minutes and then concentrated to give a crude product (145.2 g).

The crude obtained was resuspended in 600 ml of isopropyl ether with stirring overnight, before being filtered and dried so as to give a yellow solid (42.6 g). This solid was taken up in an MeOH/H$_2$O mixture (70 ml, 6/4) and concentrated aqueous ammonia was added to the solution until a pH>11 was obtained, before being extracted 3 times with dichloromethane. The combined organic phases were dried over magnesium sulfate, filtered and concentrated under vacuum so as to give a red/black solid (39.4 g). This solid was in turn taken up in dichloromethane, and the solution obtained was washed twice with water, dried over magnesium sulfate and filtered. The filtrate was treated with active carbon (5.5 g) and filtered on Celite so as to give the expected compound 4, isolated in the form of a red solid.

The spectroscopic and spectrometric analyses agree with the structure of the expected compounds 4 (nitro et nitroso).

Preparation of
1-hexyl-3-methyl-1H-pyrazole-4,5-diamine:
Compound 5

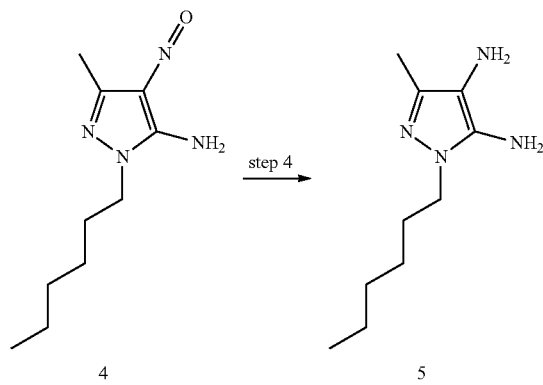

In a 2-litre three-necked reaction vessel, equipped with magnetic stirring, a thermometer, a reflux condenser and a dropping funnel, a suspension of the compound 4 (31.39 g) in ethanol (1.8 l) is prepared under an inert atmosphere, and palladium-on-charcoal (558 mg) and hydrazine (37.3 g) are added. The mixture is hydrogenated for 1 h at 70° C. and the end of the reaction is controlled by TLC (95/5 dichloromethane/methanol). The reaction medium is cooled to ambient temperature and filtered and the solid is washed with methanol. The filtrate is then concentrated so as to give the crude product which is then dissolved in ethyl acetate, and the solution obtained is washed twice with water.

The organic phase was dried over magnesium sulfate, filtered and concentrated under vacuum so as to give a yellow solid (27.4 g) which was then taken up with pentane so as to give the expected compound 5 in the form of a yellow solid (25.5 g).

The spectroscopic and spectrometric analyses agree with the structure of the expected compound 5.

Preparation of
1-hexyl-3-methyl-1H-pyrazole-4,5-diamine
hemisulfate 5A

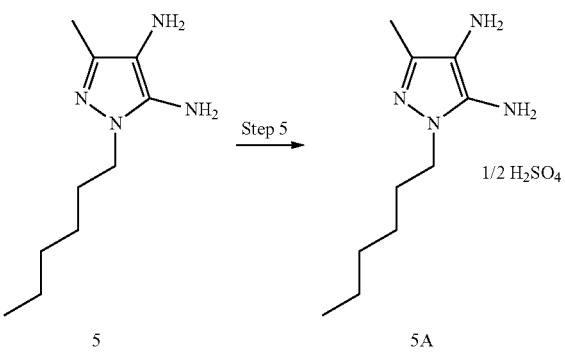

A solution of 7 g of sulfuric acid in 100 ml of a water/ethanol mixture is introduced into a round-bottomed flask equipped with magnetic stirring, and brought to 50° C.

25.5 g of 1-hexyl-3-methyl-1H-pyrazole-4,5-diamine 5 are then added and the mixture is maintained at 50° C. for 20 minutes. After concentration, the residue is triturated in 300 ml of acetonitrile so as to give a beige solid (30 g).

This solid is finally taken up with 350 ml of a mixture of methanol and water (9/1). After filtration of the suspension at 0° C. and drying until the weight is constant, 15.7 g of 1-hexyl-3-methyl-1H-pyrazole-4,5-diamine hemisulfate (5A) are obtained in the form of a pink solid.

The spectroscopic and spectrometric analyses agree with the structure of the expected compound 5A.

Process 3: (Via an Azo Intermediate)

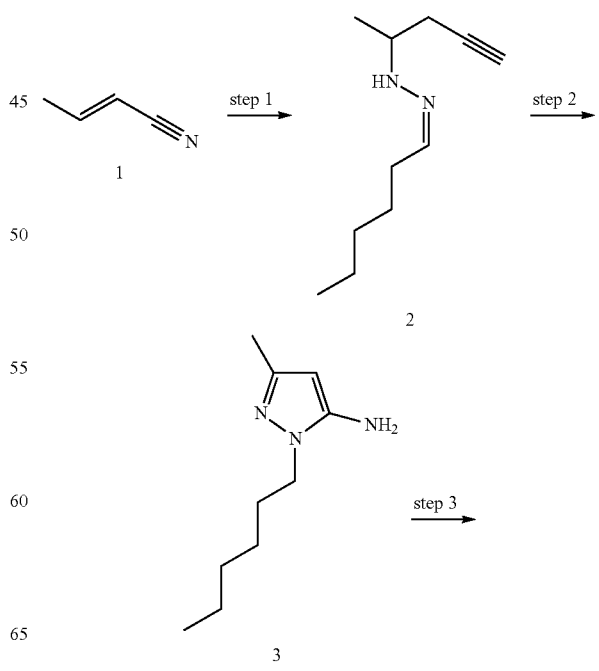

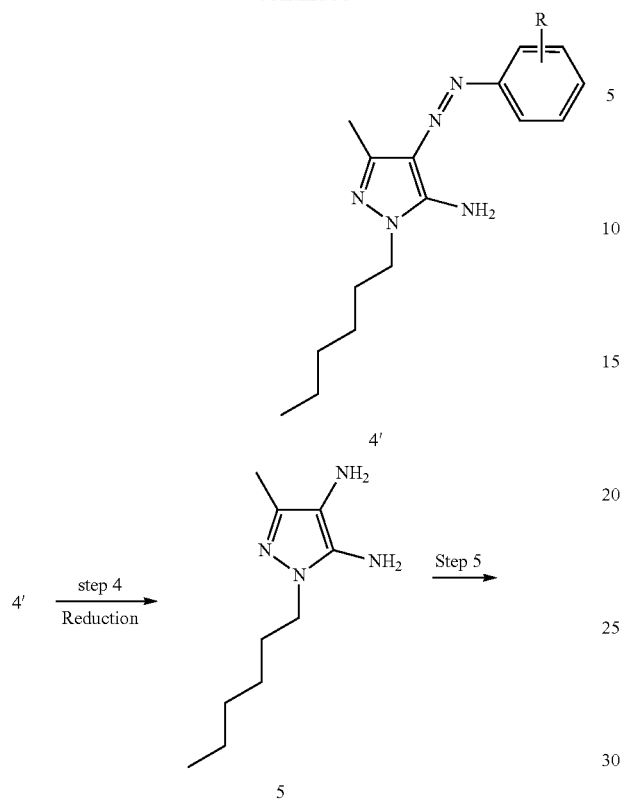

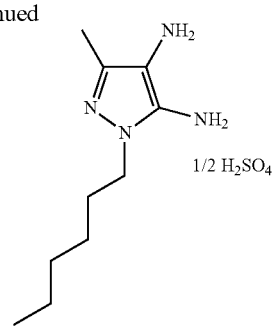

with R representing a hydrogen or halogen atom, a $(C_1\text{-}C_4)$ alkyl group, or an $SO_3R'$ group with $R'$ representing a hydrogen atom or an alkali or alkaline-earth metal, such as sodium.

The benzenediazonium salts are easily accessible by conventional methods of organic synthesis or are commercially available. Mention may for example be made of benzenediazonium halides and in particular the following commercial benzenediazoniums: benzenediazonium chloride (BENZENEDIAZONIUM CHLORIDE-100-34-5), 2-methylbenzenediazonium chloride(2-METHYL-BENZENEDIAZONIUM CHLORIDE-2028-34-4), 3-methyl-benzenediazonium chloride (3-METHYL-BENZENEDIAZONIUM CHLORIDE-2028-72-0), and para-diazobenzenesulfonic acid (P-DIAZOBENZENESULFONIC ACID, 305-80-6).

Examples of Dyeing

The following dye compositions are prepared

| Ingredients | Amount | | | |
|---|---|---|---|---|
| | comp. a | comp. b | comp. c | comp. d |
| Compound 5A | $10^{-3}$ mol | $10^{-3}$ mol | $10^{-3}$ mol | $10^{-3}$ mol |
| Resorcinol | $10^{-3}$ mol | | | |
| 3-aminophenol | | $10^{-3}$ mol | | |
| 1H-indol-6-ol | | | $10^{-3}$ mol | |
| 5-amino-2-methylphenol | | | | $10^{-3}$ mol |
| Dyeing support (1) | (*) | (*) | (*) | (*) |
| Demineralized water q.s. | 100 g | 100 g | 100 g | 100 g |
| Shade observed | beige | light fuchsia | Brown-beige | Purple-beige |

| Ingredients | Amount | | | |
|---|---|---|---|---|
| | comp. e | comp. f | comp. g | comp. h |
| Compound 5A | $10^{-3}$ mol | $10^{-3}$ mol | $10^{-3}$ mol | $10^{-3}$ mol |
| 3-6-hydroxybenzomorpholine | $10^{-3}$ mol | | | |
| 2-methyl-5-hydroxyethyl-aminophenol | | $10^{-3}$ mol | | |
| 2-amino-3-hydroxypyridine | | | $10^{-3}$ mol | |
| 3-amino-2-chloro-6-methylphenol | | | | $10^{-3}$ mol |
| Dyeing support (1) | (*) | (*) | (*) | (*) |
| Demineralized water q.s. | 100 g | 100 g | 100 g | 100 g |
| Shade observed | Chromatic violet | Vivid chromatic purple | Fuchsia | Vivid purple-violet |

-continued

| Ingredients | Amount | | | |
|---|---|---|---|---|
| | comp. i | comp. j | comp. k | comp. l |
| Compound 5A | $10^{-3}$ mol | $10^{-3}$ mol | $10^{-3}$ mol | $10^{-3}$ mol |
| 2-(2,4-Diaminophenoxy)ethanol hydrochloride | $10^{-3}$ mol | | | |
| 2-methylresorcinol | | $10^{-3}$ mol | | |
| 6-Methoxy-N2-methylpyridine-2,3-diamine hydrochloride | | | $10^{-3}$ mol | |
| 1-naphthol | | | | $10^{-3}$ mol |
| Dyeing support (1) | (*) | (*) | (*) | (*) |
| Demineralized water q.s. | 100 g | 100 g | 100 g | 100 g |
| Shade observed | Dark violet | Light beige | Vivid chromatic green | Violet |

(*): dyeing support (1) pH 9.5

| | |
|---|---|
| 96° ethyl alcohol | 20.8 g |
| 35% aqueous sodium metabisulfite solution | 0.23 g AM |
| Pentasodium salt of diethylenetriaminepentaacetic acid as an aqueous 40% solution | 0.48 g AM |
| 60% aqueous solution of $C_8$-$C_{10}$ alkyl-polyglucoside | 3.6 g AM |
| Benzyl alcohol | 2.0 g |
| Polyethylene glycol containing 8 units of ethylene oxide | 3.0 g |
| $NH_4Cl$ | 4.32 g |
| Aqueous ammonia containing 20% $NH_3$ | 2.94 g |

At the time of use, each composition is mixed with an equal weight of 20-volumes aqueous hydrogen peroxide solution (6% by weight). A final pH of 9.5 is obtained.

Each mixture obtained is applied to locks of grey hair containing 90% white hairs. After a leave-on time of 30 minutes, the locks are rinsed, washed with a standard shampoo, rinsed again and then dried, so as to obtain the various shades.

Comparative Tests hexyl-3-methyl-1H-pyrazole-4,5-diamine hemisulfate: compound 5A according to the invention hexyl-1H-pyrazole-4,5-diamine hemisulfate: Comparative The compound according to the invention and the comparative were tested in the same supports and under the same operating conditions as the previous examples.

Resistance to Light (NV-RCL CAP 54)

The locks dyed using the compositions described above were exposed to light according to the following protocol:

The dyed locks are exposed to light using a Xenotest 150S machine from the company Atlas at an average lighting level (about 1250 W/m² between 300 and 800 nm for 7 infrared filters).

The humidity level is set at 60%. The exposure time is 40 hours.

The colour of the locks was evaluated before and after exposure to light in the L*a*b* system, using a Minolta® CM 2002 spectrophotometer (Illuminant $DE_{76}$). In this L*a*b* system, L* represents the intensity of the colour, a* indicates the green/red colour axis and b* indicates the blue/yellow colour axis. The lower the value of L, the darker or more intense the colour. The higher the value of a*, the redder the shade, and the higher the value of b*, the bluer the shade.

The variation in the colour of the locks before and after exposure to light is measured by (ΔE) according to the following equation:

$$\Delta E = \sqrt{(L^*-L_0^*)^2 + (a^*-a_0^*)^2 + (b^*-b_0^*)^2}$$

In this equation, L*, a* and b* represent the values measured after exposure to light, and $L_0^*$, $a_0^*$ and $b_0^*$ represent the values measured before exposure.

The greater the ΔE value, the greater the difference in colour of the lock before and after exposure, which shows a reduced light fastness.

The results are reported in the table below

| Light Fastness | | |
|---|---|---|
| Base | coupler | $\Delta E^*_{76}$ |
| 1-hexyl-3-methyl-1H-pyrazole-4,5-diamine hemisulfate | 2-methylresorcinol | 3.42 |
| 1-hexyl-1H-pyrazole-4,5-diamine hemisulfate | | 6.56 |
| 1-hexyl-3-methyl-1H-pyrazole-4,5-diamine hemisulfate | 6-hydroxybenzomorpholine | 2.13 |
| 1-hexyl-1H-pyrazole-4,5-diamine hemisulfate | | 4.86 |
| 1-hexyl-3-methyl-1H-pyrazole-4,5-diamine hemisulfate | 2-amino-3-hydroxypyridine | 4.7 |
| 1-hexyl-1H-pyrazole-4,5-diamine hemisulfate | | 7.48 |
| 1-hexyl-3-methyl-1H-pyrazole-4,5-diamine hemisulfate | 2-({3-[(2-hydroxyethyl)amino]-2-methylphenyl}amino)ethanol | 12.57 |
| 1-hexyl-1H-pyrazole-4,5-diamine hemisulfate | | 22 |

Chromaticity

The chromaticity C* is defined according to the following equation:

$$C^* = \sqrt{a^{*2} + b^{*2}}$$

In this equation, a* and b* represent the values measured on locks of hair after colouration. The higher the C*value, the better the chromaticity of the colour.

| Base | coupler | C* |
|---|---|---|
| 1-hexyl-3-methyl-1H-pyrazole-4,5-diamine hemisulfate | 2-(2,4-diaminophenoxy)-ethanol hydrochloride | 12.19 |
| 1-hexyl-1H-pyrazole-4,5-diamine hemisulfate | | 6.49 |

It appears that the dyes of the invention, i.e. 1-hexyl-4,5-diaminopyrazole substituted in position 3, make it possible to significantly improve the persistence to light and the chromaticity of the colours obtained on the keratin fibres after application compared with the comparative dyes not substituted in position 3.

The invention claimed is:

1. A compound chosen from compounds of formula 5A below:

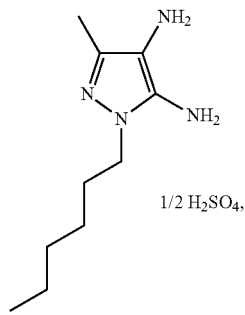

solvates thereof, or mixtures thereof.

2. A composition for oxidation dyeing of keratin fibers, wherein the composition comprises i) at least one compound chosen from compounds of formula:

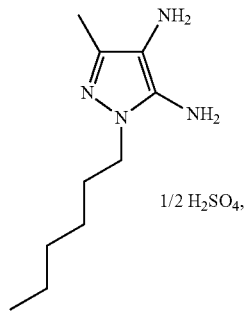

solvates thereof, or mixtures thereof; and iii) at least one coupling agent.

3. The composition according to claim 2, wherein the composition further comprises ii) at least one additional oxidation base chosen from para-phenylenediamines, bis-phenylalkylenediamines, para-aminophenols, ortho-aminophenols, or heterocyclic bases different from the compounds of formula 5A.

4. The composition according to claim 2, wherein the composition further comprises ii) at least one additional oxidation base chosen from para-phenylenediamine, para-toluenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-methoxymethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene, 3-hydroxy-1-(4'-aminophenyl)pyrrolidine, addition salts thereof with an acid, or mixtures thereof.

5. The composition according to claim 2, wherein the composition further comprises ii) at least one additional oxidation base chosen from N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine, 1,8-bis(2,5-diaminophenoxy)-3,6-dioxaoctane, addition salts thereof, or mixtures thereof.

6. The composition according to claim 2, wherein the composition further comprises ii) at least one additional oxidation base chosen from para-aminophenol, 4-amino-3-methylphenol, 4-amino-3-fluorophenol, 4-amino-3-chlorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethyl-aminomethyl)phenol, 4-amino-2-fluorophenol, addition salts thereof with an acid, or mixtures thereof.

7. The composition according to claim 2, wherein the composition further comprises ii) at least one additional oxidation base chosen from 2-aminophenol, 2-amino-5-methylphenol, 2-amino-6-methylphenol, 5-acetamido-2-aminophenol, addition salts thereof, or mixtures thereof.

8. The composition according to claim 2, wherein the composition further comprises ii) at least one additional oxidation base chosen from 2,5-diaminopyridine, 2-(4-methoxyphenyl)amino-3-aminopyridine, 3,4-diaminopyridine, 3-aminopyrazolo[1,5-a]pyridine, pyrazolo[1,5-a]pyrid-3-ylamine, 2-acetylaminopyrazolo[1,5-a]pyrid-3-ylamine, 2-morphohn-4-ylpyrazolo[1,5-a]pyrid-3-ylamine, 3-aminopyrazolo[1,5-a]pyridine-2-carboxylic acid, 2-methoxypyrazolo[1,5-a]pyrid-3-ylamine, (3-aminopyrazolo[1,5-a]pyrid-7-yl)methanol, 2-(3-aminopyrazolo[1,5-a]pyrid-5-yl)ethanol, 2-(3-aminopyrazolo[1,5-a]pyrid-7-yl)ethanol, (3-aminopyrazolo[1,5-a]pyrid-2-yl)methanol, 3,6-diaminopyrazolo[1,5-a]pyridine, 3,4-diaminopyrazolo[1,5-a]pyridine, pyrazolo[1,5-a]pyridine-3,7-diamine, 7-morpholin-4-ylpyrazolo[1,5-a]pyrid-3-ylamine, pyrazolo[1,5-a]pyridine-3,5-diamine, 5-morpholin-4-ylpyrazolo[1,5-a]pyrid-3-ylamine, 2-[(3-aminopyrazolo[1,5-a]pyrid-5-yl)(2-hydroxyethyl)-amino]ethanol, 2-[(3-aminopyrazolo[1,5-a]pyrid-7-yl)(2-hydroxyethyl)amino]ethanol, 3-aminopyrazolo[1,5-a]5yridine-5-ol, 3-aminopyrazolo[1,5-a]5yridine-4-ol, 3-aminopyrazolo[1,5-a]5yridine-6-ol, 3-aminopyrazolo[1,5-a]5yridine-7-ol, 2-β-hydroxyethoxy-3-amino-pyrazolo[1,5-a]pyridine; 2-(4-dimethylpiperazinium-1-yl)-3-amino-pyrazolo[1,5-a]pyridine, 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine, 4,5-diamino-1- methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole, 3,5-diamino-4-(β-hydroxyethyl)amino-1-methylpyrazole, addition salts thereof, or mixtures thereof.

9. The composition according to claim 2, wherein the iii) at least one coupling agent is chosen from 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene, 2,6-bis(β-hydroxyethylamino)toluene, 6-hydroxyindoline, 2,6-dihydroxy-4-methylpyridine, 1-H-3-methylpyrazol-5-one, 1-phenyl-3-methylpyrazol-5-one, 2,6-dimethylpyrazolo[1,5-b]-1,2,4-triazole, 2,6-dimethyl[3,2-c]-1,2,4-triazole and 6-methylpyrazolo[1,5-a]benzimidazole, 2-methyl-5-aminophenol, 5-N-(β-hydroxyethyl)amino-2-methylphenol, 3-aminophenol, 3-amino-2-chloro-6-methylphenol, addition salts thereof with an acid, or mixtures thereof.

10. The composition according to claim 2, wherein the iii) at least one coupling agent is chosen from compounds of formulae (II) and (II'):

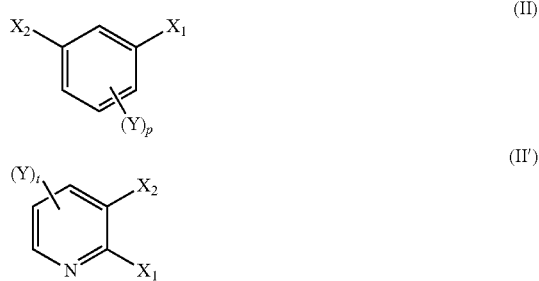

organic or mineral acid or base salts thereof, solvates thereof, or mixtures thereof;
wherein:
$X_1$ and $X_2$, which may be identical or different, represent a group chosen from hydroxyl, (di)($C_1$-$C_6$)(alkyl)amino, or (di)hydroxy($C_1$-$C_6$)alkylamino;

Y represents a hydrogen atom or ($C_1$-$C_6$)(hydroxy)alkyl, or two adjacent substituents Y and $X_1$ and/or Y and $X_2$ form, together with the carbon atoms which bear them, an optionally substituted heterocyclic group, or else two adjacent substituents Y and $X_1$ form, together with the carbon atoms which bear them, a morpholinyl group optionally substituted with a ($C_1$-$C_4$)alkyl group;
p is 1, 2, 3 or 4;
t is 1, 2 or 3;
it being understood that, when p or t is greater than or equal to 2, the Y groups are identical to or different from one another.

11. The composition according to claim 2, wherein the iii) at least one coupling agent is chosen from the compounds of formulae ($II_a$) and ($II'_a$):

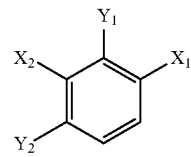

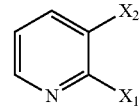

organic or mineral acid or base salts thereof, solvates thereof, or mixtures thereof;
wherein:
$X_1$ and/or $X_2$ represent(s) a hydroxyl, amino, or (hydroxy)alkylamino group;
$Y_1$ represents a hydrogen atom or a ($C_1$-$C_6$)alkyl group;
$Y_2$ represents a hydrogen atom, or forms, with the substituent $Y_2$, an optionally substituted heterocycle.

12. A method for dyeing keratin fibers, comprising applying the composition of claim 2 to the keratin fibers.

13. The method according to claim 12, wherein a color of the composition is revealed at acid, neutral, or alkaline pH by an oxidizing agent which is added to the dye composition at the time of use or which is present in an oxidizing composition applied to the keratin fibers simultaneously or sequentially with the application of the composition of claim 10.

14. The method according to claim 13, wherein the oxidizing agent is chosen from hydrogen peroxide, urea peroxide, alkali metal bromates, persalts, peracids, oxidase enzymes, or mixtures thereof.

15. A multi-compartment device, wherein the device comprises a first compartment comprising a dye composition as defined in claim 2 and a second compartment comprising an oxidizing composition.

16. The composition according to claim 2, wherein the total amount of compounds chosen from compounds of formula 5A and solvates thereof ranges from 0.001% to 10% by weight, relative to the total weight of the composition.

17. The composition according to claim 2, wherein the total amount of compounds chosen from compounds of formula 5A and solvates thereof ranges from 0.1% to 3% by weight, relative to the total weight of the composition.

18. The composition according to claim 2, wherein the total amount of coupling agents ranges from 0.001% to 10% by weight, relative to the total weight of the composition.

19. The composition according to claim 3, wherein the total amount of additional oxidation bases chosen from para-phenylenediamines, bis-phenylalkylenediamines, para-aminophenols, ortho-aminophenols, or heterocyclic bases different from compounds of formula 5A ranges from 0.001% to 10% by weight, relative to the total weight of the composition.

20. The composition according to claim 2, further comprising at least one additional component chosen from direct dyes; surfactants chosen from anionic, cationic, non-ionic, amphoteric, or zwitterionic surfactants; polymers chosen from anionic, cationic, non-ionic, amphoteric, or zwitterionic polymers; thickeners; antioxidants; penetrants; sequestrants; fragrances; buffers; dispersants; conditioning agents; film-forming agents; ceramides; preserving agents; opacifiers; or mixtures of two or more thereof.

* * * * *

UNITED STATES PATENT AND TRADEMARK OFFICE
CERTIFICATE OF CORRECTION

PATENT NO.        : 11,555,017 B2
APPLICATION NO.   : 16/095816
DATED             : January 17, 2023
INVENTOR(S)       : Aziz Fadli It is certified that error appears in the above-identified patent and that said Letters Patent is hereby corrected as shown below:

In the Claims

Claim 8, Column 30, Line 60, please change "[1,5-a]5yridine-5-ol" to -- [1,5-a]pyridine-5-ol --;

Claim 8, Column 30, Line 61, please change "a]5yridine" to -- a]pyridine -- and change "[1,5-a]5yridine" to -- [1,5-a]pyridine --; and Claim 8, Column 30, Line 62, please change "[1,5-a]5yridine" to -- [1,5-a]pyridine --.

Signed and Sealed this
Twenty-eighth Day of February, 2023

*Katherine Kelly Vidal*

Katherine Kelly Vidal
*Director of the United States Patent and Trademark Office*